United States Patent [19]

Margison

[11] Patent Number: 5,419,336
[45] Date of Patent: May 30, 1995

[54] HEART BEAT MONITORING

[76] Inventor: Stephen Margison, 25 St. Mary's Hall Road, Crumpsall, Manchester M8 6BG, Great Britain

[21] Appl. No.: 961,688
[22] PCT Filed: May 10, 1991
[86] PCT No.: PCT/GB91/00745
§ 371 Date: Jan. 6, 1993
§ 102(e) Date: Jan. 6, 1993
[87] PCT Pub. No.: WO91/16851
PCT Pub. Date: Nov. 14, 1991

[30] Foreign Application Priority Data

May 10, 1990 [GB] United Kingdom ............... 9010455

[51] Int. Cl.6 ................................ A61B 5/04
[52] U.S. Cl. ................................ 128/696; 128/903
[58] Field of Search .......... 128/633, 664, 670, 672, 128/689, 690, 710, 903, 904; 607/32, 60

[56] References Cited

U.S. PATENT DOCUMENTS

| 3,910,257 | 10/1973 | Fletcher et al. | 128/670 |
| 4,151,407 | 4/1979 | McBride et al. | 359/158 |
| 4,677,982 | 7/1987 | Llinas et al. | 128/664 |
| 4,987,902 | 1/1991 | Couche | 128/696 |
| 5,038,782 | 8/1991 | Gevins et al. | 128/644 |
| 5,307,817 | 5/1994 | Guggenbuhl et al. | 128/710 |

OTHER PUBLICATIONS

Weller "Modulation Scheme Suitable for Infra-Red Biotelemetry" Electronics Letters, vol. 21, No. 14, 4 Jul. 1985 pp. 601–602.

Primary Examiner—William E. Kamm
Assistant Examiner—Marianne Arker
Attorney, Agent, or Firm—Larson and Taylor

[57] ABSTRACT

An infra-red transmitter comprising transducer means (10) for sensing heart beat and producing a detectable electrical signal (10P); infra-red transmission means (28) that is energisable from a battery (30); signal processing means (14–20) that is responsive to transducer output signals representative of heart beats, and serves to produce therefrom short pulses (20P); and means (32–36) responsive to said short pulses (20P) for gating electrical energy originating with said battery to the infra-red transmission means (28) at voltage(s) and duration(s) that secure detectable penetration of a layer of clothing along with acceptably low battery power consumption.

9 Claims, 2 Drawing Sheets

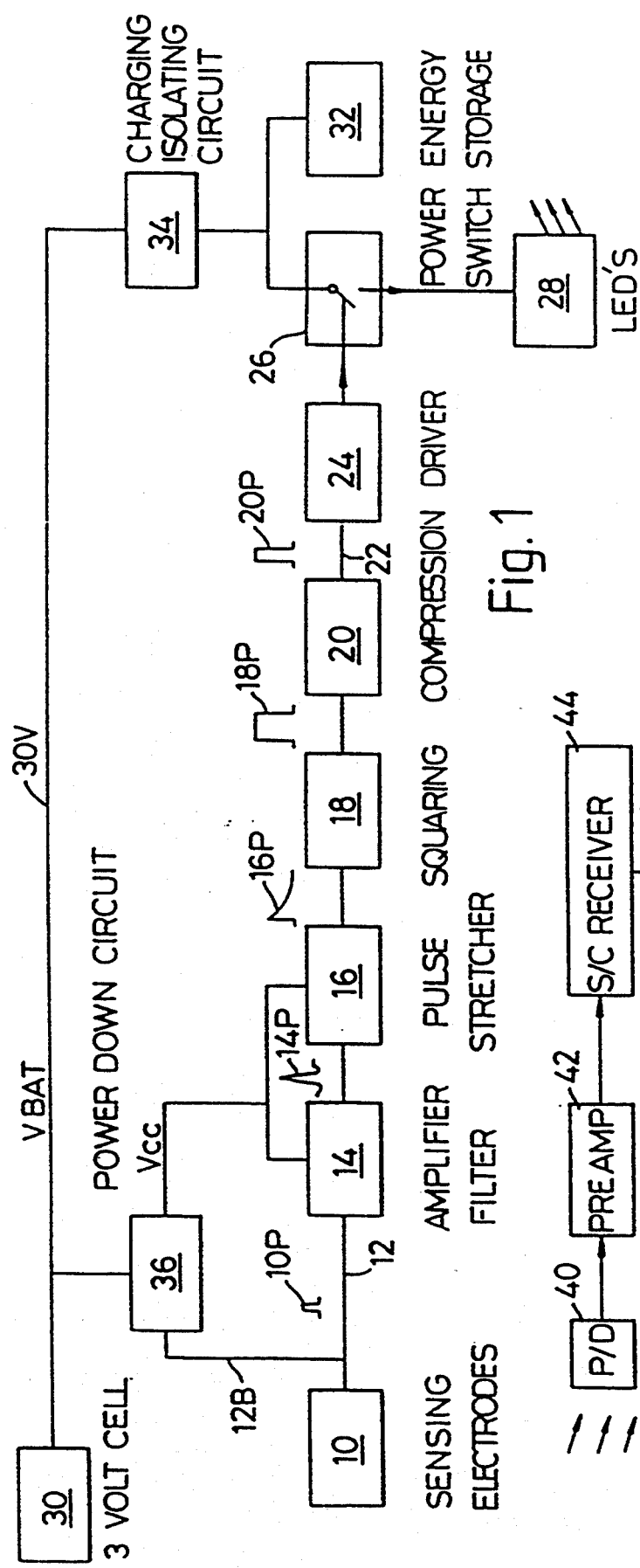

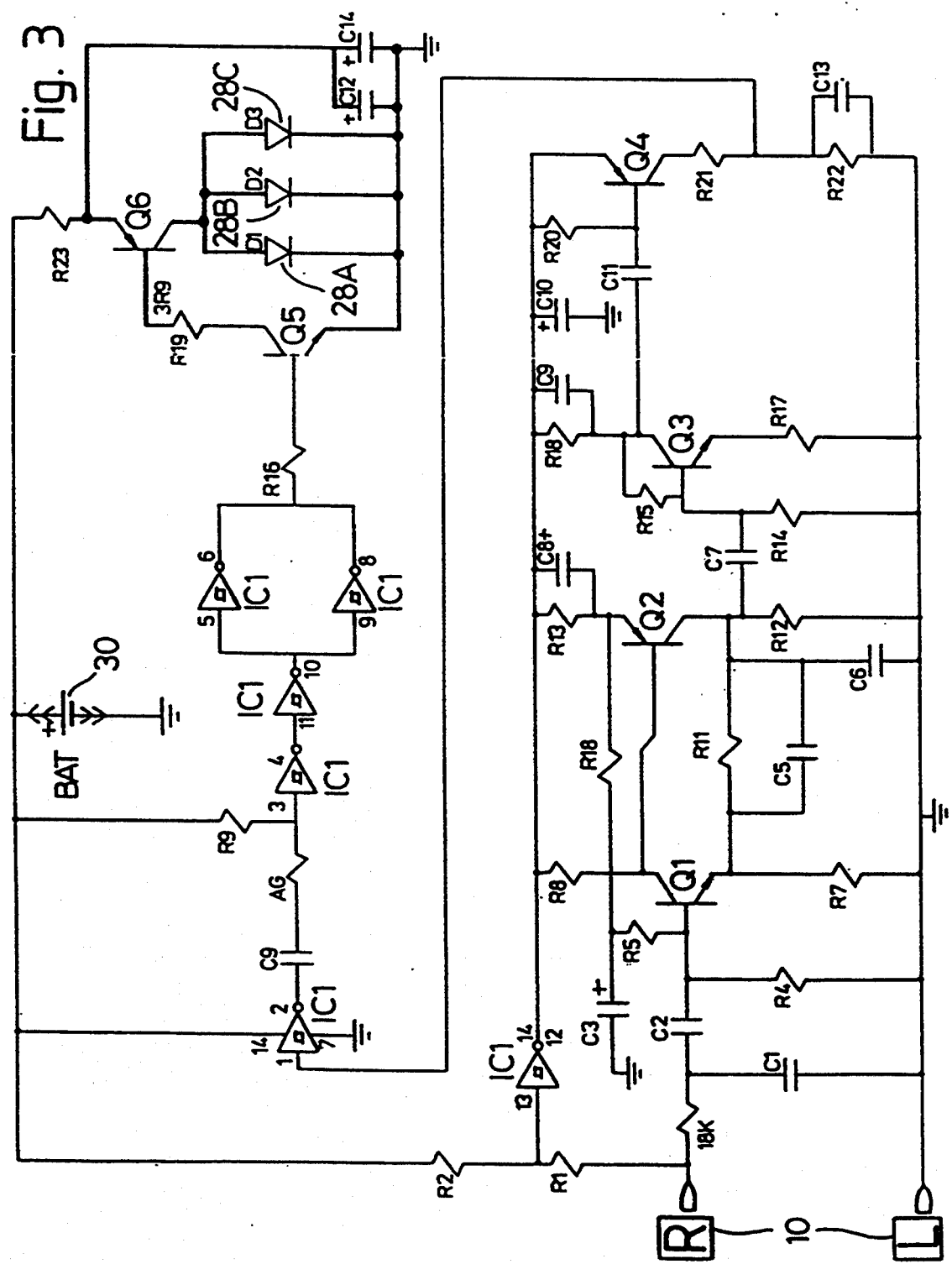

HEART BEAT MONITORING

BACKGROUND OF THE INVENTION

1. Field of the Invention

The invention relates to monitoring heart beat or pulse rate.

2. The Prior Art

Conventionally, such monitoring is done using electro-magnetic RF techniques, typically using a harness and with signal transmission through at least one layer of clothing, often a T-shirt. Use of radio frequency, typically about 800 KHz, can give most undesirable interference effects.

SUMMARY OF THE INVENTION

It is an object of the invention to provide an alternative system free of such possible interference effects; specifically do so utilising infra-red transmission and reception.

Such transmitter/reception systems are, of course, well known from remote controls for domestic and other electronic equipment, such as televisions and audio systems or motor vehicle locking/alarm systems. However, in all such cases, the infra-red source or transmitter is invariably exposed and it has been established that application of such existing infra-red transmission/reception technology to heart beat monitoring is incapable reliably of penetrating a layer of clothing.

Accordingly, it is a particular object of this invention to produce an infra-red communication system that is free of such problems, i.e. affectively provides compatibility of utility with existing RF systems, including capability for a reasonable operating life of practical batteries for the transmitter.

According to the invention there is provided an infra-red transmitter comprising transducer means for sensing heart beat and producing a detectable electrical signal, infra red transmission means energisable from a battery, and signal processing means responsive to transducer output signals representative of heart beats, for producing therefrom short pulses that serve to gate electrical energy originating with said battery to the infra-red transmission means at voltage and duration that secure detectable penetration of a layer of clothing along with acceptably low battery power consumption.

Embodiments of this invention are capable of implementation using conventional heart beat sensing transducer means, and conventional infra-red receiver means namely photodiodes or the like; and the latter will usually be coupled through an amplifier/receiver producing signals for a microprocessor feeding suitable recording and/or display means.

Moreover, successful operation has been achieved using conventional light emitting diodes (LEDs) as the infra-red transmission means, and 3-volt lithism batteries.

In order to achieve sufficient intensity of infra-red transmission, energisation of LEDs have been at order of magnitude greater than that normal for exposed LED remote controller systems, actually as high as 1.5 amp or more through each of a parallel bank or set of LEDs.

However, in order to sustain useful battery life, gate pulse widths controlling such LED energisation have been set below 100 micro-seconds, actually about 50 micro-seconds. That, of course compares with LED energisation currents of milliamps or tens of milliamps for energisation of otherwise exposed remote controller systems, i.e. as much as two or three orders of magnitude higher energisation, and with touch-operated energisation intervals of up to seconds, i.e. as little as two or three orders of magnitude less energisation time, and thus an entirely different approach to infra-red communication systems.

It is not, of course, to be taken that pulse widths longer than 100 micro-seconds are wholly impractical for battery-powered devices. The type of battery concerned can be taken into account, including as to whether it is re-chargeable, all within the bounds of tolerance of battery size and/or frequency of required re-charging. However, it is not envisaged that pulse-widths longer than a few milliseconds, perhaps up to 5, could be tolerable in practice, though an order of magnitude less would improve tolerable practicality. The advantages of reducing pulse widths within practical and economic considerations should be appreciated, particularly as specifically to be described herein.

The desired combination of high levels and short intervals of energisations relates to mark-space ratios of actual power consumption that are compatible with useful battery life, i.e. low power consumption. In most preferred embodiments, typical mark-space ratios amount to one in hundreds, preferably thousands. For example, at 1.5 amps peak and 50 micro-second energisation durations, mark-space ratio is only one in 5,000 with a heart rate as high as 240 per minute, which is a reasonably practical maximum for monitoring even the relatively unfit during periods of quite heavy physical effort/exercise. Actual demands on the battery will be virtually in inverse relation to said mark-space by virtue of using storage means that builds up charge between drive pulses but the overall battery demand will be consistent therewith.

Preferred signal processing and conditioning means for controlling driving infra-red transmission means, i.e. generating drive gating pulses, comprises successive amplifier (conveniently gains of over 1000), pulse stretching (conveniently as a sawtooth) pulse squaring, and squared pulse compression stages to give a reliable clean gating pulse.

Relatively thick conductor tracking is preferred and advantageous for charge storage and output driver stages of the transmitter.

BRIEF DESCRIPTION OF THE DRAWINGS

Specific implementation for the invention will now be described, by way of example, with reference to the accompanying drawings, in which:

FIG. 1 is a block-circuit diagram of an infra-red transmitter;

FIG. 2 is a block-circuit diagram of an infra-red receiver/recorder/display system; and FIG. 3 is a more detailed circuit diagram for an infra-red transmitter.

DESCRIPTION OF THE PREFERRED EMBODIMENTS

In the drawings, referring first to FIGS. 1 and 2, heart beat sensing electrodes 10 produce an electrical pulse 10P on line 12 to signal conditioning and processing circuitry 14–20 producing a short duration pulse 20P on line 23 applied to driver 24 for power switching means 26 operative to release energy to infra-red transmitting stage 28.

The signal conditioning and processing circuitry 14–20 comprises an amplifier filter stage 12 producing an enhanced and cleaned heart-beat representing pulse 14P going to a pulse stretching stage 16 producing a saw-tooth pulse 16P going to a pulse squaring stage is producing a stretched square pulse 18P going to a pulse compression stage 20 producing the output pulse 20P of short duration.

This progression of stages assures reliable and accurate control of the ultimate pulse 20P for a very wide range of quality of signals detected by the electrodes 10.

The ultimate source of electrical power is a battery 30, but actual supply to the infra-red transmission stage 28, typically a bank or set of LEDs, is a charge storage stage 32, fed from battery positive voltage line 30V through a one-way charging/isolating stage 34 throughout intervals between driver control pulses 20P, usually plus response intervals of the driver and switching stages 24 and 26.

Appropriate supply (Vcc) and bias voltages for the stages 14–26, particularly Vcc voltage for stages 14 and 16, are derived indirectly from the battery voltage line 30V by way of a voltage control stage 36 shown operative between quiescent and power-on conditions in response to signals from sensing electrode output line 12 are over branch 12B.

Stages 34 and 36 are effectively battery management provisions effective to minimise battery power depletion and thus maximise battery life.

FIG. 2 shows a typical receiver having a photodiode or photo-transistor detection stage 40 feeding a preamplifier 42 and a receiver stage 44 that can usefully operate on a switched carrier basis and may well incorporate the preamplifier stage shown separately at 42. Such a receiver stage 44 will produce an output on line 46 that consists of an oscillation carrier signal only for durations of energisation of the detection stage 40 resulting on useable output signals to the preamplifier 42. That carrier signal burst is shown applied to a micro-processor interface or port 48 for a microprocessor 50 programmed to produce either or both of signals for a recorder 52 shown applied over a conventional RS232 interface 54 and signals for a display 56, conveniently a liquid crystal display producing a decimal digital reading.

Basic operating conditions and parameters for the transmitter of FIG. 1 have been discussed above, and a practical circuit is shown in FIG. 3 making use of a plural Schmitt inverter gate integrated circuit IC1 whose component gates are shown so labelled at various positions of FIG. 3.

Heart beat detection electrodes, are shown as 10R and 10L feeding a two stage direct current coupled amplifier utilising complementary first and second transistors Q1 and Q2 with signal feedback via resistor R11 and capacitor C5. The use of complementary first and second transistors Q1 and Q2 reduces sensitivity to supply voltage variation or noise. Direct current bias is maintained by resistive feedback from the emitter of the second transistor Q2 to the base of the first transistor Q1 over resistors R5 and R18. Capacitor C3 serves to decouple signals that could otherwise feed from the supply to the base of the first transistor Q1 along the bias chain to the second transistor Q2. If third transistor Q3 adds further gain and shapes frequency response to give desired overall voltage gain typically of over 1000 at the collector of the third transistor Q3. Peak frequency response at about 15 Hz rolling off to a off peak value at 50 Hz, and overall gains of 1100 to 1500 for a supply range of 2.7 to 3.2 volts have been used successfully in experiments.

The specific circuitry thus far described for FIG. 3 effectively constitutes the amplifier and filter stage 14 of FIG. 1, and pulse stretching is achieved at collector load represented by parallel combination of resistor R22 and capacitor C13 for a fourth transistor Q4. Squaring followed by compression by differentiation is achieved by five Schmitt inverter gates of IC1 arranged as shown in the upper part of FIG. 3, i.e. three cascaded gates with capacitor C9 and resistors R6 and R7 between the first and second gates and the third gate feeding the fourth and fifth gates connected in parallel feed for a squared compressed output pulse to driver and switching sections involving complementary fifth and sixth transistors Q5 and Q6.

In fact, both of the fifth and sixth transistors Q5 and Q6 operate all switches and are part of a thick-tracked output stage also including a parallel pair of charge storage capacitors C12, C14 fed from the battery 30 over a resistor R23. The feed resistor R23 is chosen to be as large as possible and yet fully charge the storage capacitors C12, C11 during minimum intervals between heart beats, which will permit over 200 milliseconds each, i.e. for a heart beat rate of 220 per minute. Then, an average power take off from the battery of about 1 milliamp during operation is readily achieved and is well within battery discharge specificator for a 3-volt lithium battery rated at 140 milliamp/hour.

Base drive for the fifth transistor Q5 is shared by a two parallel connected Schmitt inverter gates and can give a total drive of about 4 milliamps. A positive going compressed pulse, typically of 50 microsecond duration, applied to the base of the fifth transistor Q5 switches on the transistor Q6. The latter has a low gain, typical about ten, and requires substantial base current flow, conveniently up to about 500 milliamp, to saturate it. Total collector current flow for the sixth transistor Q6 is very high relative to normal drive for a parallel bank of three LEDs 28A,B,C and is usefully about 4.5 amp to give about 1.5 amp drive for each of the LEDs 28 A,B,C.

In practice, current sharing by the LEDs 28 A,B,C is likely to be unequal and, whilst the circuitry hereof would operate with only one LED, there are advantages in using more, for example to compensate for aging effects, producing a broader infra-red emission beam angle to reduce directional sensitivity for the receiver, and allow one or more (but not all) of the LEDs to be impenetrably marked.

Achieving the high peak current output drive requirement is much improved by careful attention to Avoiding large voltage drops in printed circuit conducting tracks, which are preferably relatively thick as mentioned above, and as indicated in FIG. 3. For similar reasons the storage capacitors C12 and C14 are preferably of low effective series resistance type.

The LED drive control pulse widths of 100 microsecond or less, typically 50 microsecond or less within the limits of response times of emitting LEDs ant receiving photodiodes or phototransistors, power consumption is low despite taking as much as 4.5 amp or more at each heart beat. The amplifier stages using transistors Q1 to Q3 can draw a quiescent current of only about 50 microamps and are only powered at all when direct current resistance between chest electrodes 10R and 10L falls below a prescribed value typically about 5 Mohm, thus providing an automatic on-off facility. Taking a maximum exercise heart rate of about 220 per minute, effective overall current flow from the battery can rise, but conveniently not to more than 1 milliamp, and current consumption is actually close to directly proportional to heart rate. In the 'off' state, current consumption is almost negligible being due only to leakage at the output transistors Q5, Q6 and quiescent current in the Schmitt inverter gate integrated circuit IC1. A total leakage/quiescent current flow of under 1 microamp is achievable and gives the transmitter a good operating and "shelf" life. Battery life for the above mentioned 3-volt lithium type rated and 140 mAh can be expected to exceed 120 hours even based on a consistently high heart rate of 220 per minute, and should be longer as the average should be rather lower.

We claim:

1. An infra-red transmitter comprising
   transducer means for sensing a heart beat and for producing a detectable electrical transducer output signal in response to sensing a heart beat;
   signal processing means for, responsive to the transducer output signals representative of heart beats, producing therefrom short pulses;
   infra-red transmission means for transmitting infrared radiation that penetrate of a layer of clothing;
   a battery for energizing said infra-red transmission means;
   and gating means responsive to said short pulses for gating electrical energy originating with said battery means to the infra-red transmission means;
   the electrical energy having voltages and durations that penetrates a layer of clothing at an acceptable low battery power consumption.

2. An infra-red transmitter according to claim 1, wherein the signal processing means includes first pulse producing means for producing pulses, pulse stretching and squaring means for stretching and squaring said pulses, and pulse compression means for compressing said squared pulses to produce said short pulses.

3. An infra-red transmitter according to claim 1 wherein the gating means responsive to said short pulses gates the electrical energy to produce quiescence and power-on conditions and includes charge storage means for storing charge, unidirectional charging isolator means for isolating the charge storage means from the battery, and a voltage control stage operative between said quiescence and power-on conditions.

4. An infra-red transmitter according to claim 1, wherein said battery is of 3-volt lithium type.

5. An infra-red transmitter according to claim 1 wherein the transmission means comprises at least one light emitting diode.

6. An infra-red transmitter according to claim 5, wherein the transmission means comprises a bank of three light emitting diodes.

7. An infra-red transmitter according to claim 5 herein the at least one light emitting diode has a energisation level, said level being at least 1.5 amp.

8. An infra-red transmitter according to claim 7 wherein said durations of said gated electrical energy for said energisation levels are below 100 microseconds.

9. Heart beat monitoring apparatus comprising:
   an infra-red detector; and an infra-red transmitter comprising
   transducer means for sensing a heart beat and for producing a detectable electrical transducer output signal in response to sensing a heart beat;
   signal processing means for, responsive to the transducer output signals representative of heart beats, producing therefrom short pulses;
   infra-red transmission means for transmitting to said infra-red detector infrared radiation that penetrates of a layer of clothing;
   a battery means for energizing said infra-red transmission means;
   gating means responsive to said short pulses for gating electrical energy originating with said battery to the infra-red transmission means;
   gate electrical energy gated by said gating means having voltages and durations that penetrates a layer of clothing at an acceptable low battery power consumption.

* * * * *